United States Patent [19]

Oishi et al.

[11] Patent Number: 4,840,484
[45] Date of Patent: Jun. 20, 1989

[54] ATOMIC ABSORPTION SPECTROPHOTOMETER WITH FURNACE AT PRESSURE EQUAL OR NEAR LIGHT SOURCE PRESSURE

[75] Inventors: Konosuke Oishi, Mito; Toyoharu Okumoto, Katsuta; Hayato Tobe, Mito; Masamichi Tsukada, Ibaraki, all of Japan

[73] Assignee: Hitachi, Ltd., Tokyo, Japan

[21] Appl. No.: 175,320

[22] Filed: Mar. 30, 1988

[30] Foreign Application Priority Data

Mar. 30, 1987 [JP] Japan .................................. 62-76562

[51] Int. Cl.⁴ .......................................... G01N 21/74
[52] U.S. Cl. ..................................................... 356/312
[58] Field of Search .......................................... 356/312

[56] References Cited

U.S. PATENT DOCUMENTS 3,591,289  7/1971  Donega et al. ..................... 356/312
4,098,554  7/1978  Huber et al. ........................ 356/312

FOREIGN PATENT DOCUMENTS 2159028  11/1985  United Kingdom ................ 356/312

OTHER PUBLICATIONS

Wagenaar et al, Spectrochimica Acta, vol. 23B, 1973, pp. 157, 162, 163, & 169.
Yasuda, Analytical Chemistry, vol. 38, 1966, pp. 592, 595–597.
Hollander et al, Combustion and Flame, vol. 13, 1969, pp. 63–65 & 68.

Primary Examiner—Vincent P. McGraw
Attorney, Agent, or Firm—Antonelli, Terry & Wands

[57] ABSTRACT

In an atomic absorption spectrophotometer including an electric furnace for drying and ashing a liquid sample to be analyzed and then atomizing the sample to generate atomic vapor, a low-pressure lamp for emitting light having a spectrum of an element to be analyzed onto the atomic vapor atomized in the electric furnace, a monochromator for splitting the transmitted light from the electric furnace and selecting a wavelength of an atomic absorption line absorbed by the element to be analyzed, and a signal processing unit for performing signal processing on the light having the selected wavelength supplied from the monochromator, the electric furnace is an airtight mechanism for maintaining airtightness of the inside of the electric furnace and an evacuation unit for evacuating the inside of the electric furnace to a pressure equal to the pressure inside the lamp.

7 Claims, 5 Drawing Sheets

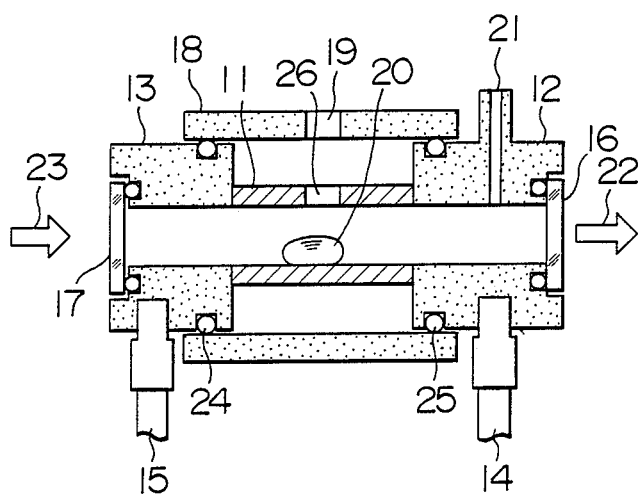
FIG. 1
PRIOR ART
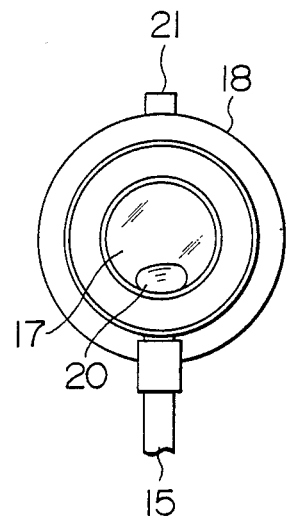
FIG. 2
PRIOR ART
FIG. 3
PRIOR ART
| STAGE | TEMPERATURE (°C) | TIME (sec) |
|---|---|---|
| DRYING | 90 | 60 |
| ASHING | 600 | 10 |
| ATOMIZING | 2800 | 10 |
| TOTAL TIME | | 80 |

FIG. 6
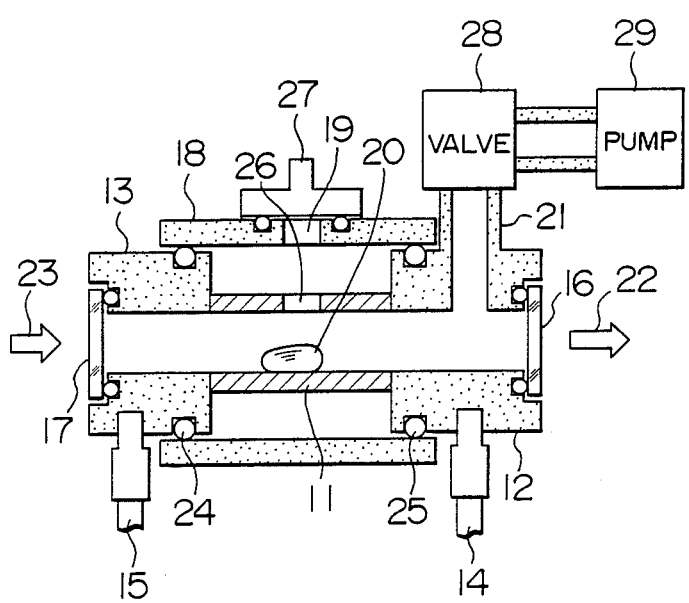
FIG. 7
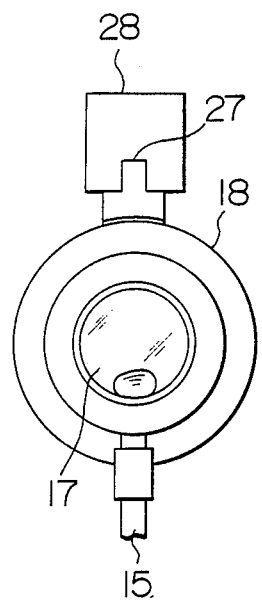
FIG. 8
| STAGE | TEMPERATURE (°C) | TIME (sec) |
|---|---|---|
| DRYING | 90 | 16 |
| ASHING | 600 | 4 |
| ATOMIZING | 2800 | 8 |
| TOTAL TIME (sec) | | 28 |

… 1

ATOMIC ABSORPTION SPECTROPHOTOMETER WITH FURNACE AT PRESSURE EQUAL OR NEAR LIGHT SOURCE PRESSURE

BACKGROUND OF THE INVENTION

The present invention relates to an atomic absorption spectrophotometer and in particular to an atomic absorption spectrophotometer adapted to analyze microelements dissolved in a solution sample.

In accordance with the prior art of this field, for example, as shown in U.S. Pat. No. 4,098,554, light emitted from a hollow cathode lamp serving as a light source is led into an electric furnace. In this electric furnace, the solution sample is dried, ashed and atomized, and light from the light source is radiated on the atomized vapor to cause atomic absorption. Atomic absorption lines of the light transmitted through the electric furnace without being absorbed are selected by a monochromator and processed by a detection system. Numercal values proportionate to the densities of elements to be analyzed in the sample are thus obtained.

The structure of a conventional electric furnace used in such an atomic absorption spectrophotometer is shown in FIGS. 1 and 2.

In FIGS. 1 and 2, a cylindrical heating material 11 is put between a right-hand electrode 12 and a left-hand electrode 13 and electrically connected to these electrodes. A current is supplied through a right-hand terminal 14 and a left-hand terminal 15 to heat the cylindrical heating material 11 to a needed temperature.

The right-hand electrode 12 has a window 16 comprising a quartz material, for example, and transmitting a light ray 22 used for the atomic absorption measurement. The left-hand electrode 13 also has a window 17 comprising a quartz material for the incidence of a measuring light ray 23. A cylinder 18 comprising an insulator is put on the right-hand electrode 12 and the left-hand electrode 13. Airtightness of the contacting portion is maintained by O-rings 24 and 25. The right-hand electrode 12 has a tube 21 for introducing inert gas, through which argon gas, for example, is introduced. The central part of the cylinder 18 has an opening 19 for introducing a sample to be analyzed. The cylindrical heating material 11 also has an opening 26 which is coaxial with the above described opening. A liquid drop 20 of 20 $\mu$l, for example, is injected into the inside of the cylindrical heating material 11 via the above described openings 19 and 26 by using a micro-syringe, for example. Dried argon gas of a constant flow rate flows in via the tube 21 and flows out via the openings 26 and 19. Air within the cylindrical heating material 11 is thus expelled. As a result, reaction of the cylindrical heating material 11, heated to as high as 3,000° C. reacts with oxygen and wasted of the material are prevented.

As the cylindrical heating material 11 shown in FIGS. 1 and 2, a small cylinder, which is 40 mm in length, 5 mm in internal diameter, and 8 mm in external diameter, comprising a graphite material of high purity has heretofore been used.

When a current of 400 amperes with AC 12 volts is supplied to this cylindrical heating material 11, its surface temperature reaches approximately 300° C. If oxygen gas exists under this state, the cylindrical heating material violently reacts with the oxygen gas to produce carbonic acid gas and be wasted. In the actual analyzing operation, the relationship between the current supplied to the cylindrical heating material 11 and the temperature is derived beforehand, and a predetermined heating program is made. The cylindrical heating material 11 is then heated in accordance with the predetermined heating program.

FIG. 3 shows an example of the heating program for heating the electric furnace of FIG. 1.

The sample water drop 20 of, say, 20 $\mu$l shown in FIG. 2 is heated by the heating program shown in FIG. 3 as described below.

(a) Drying stage: The temperature is kept at 90° C. for 60 seconds to evaporate water used as a solvent and to perform drying.

(b) Ashing stage: The sample is heated to a temperature of 600° C. for 10 seconds to ash organic matters included in the dried solute.

(c) Subsequent atomizing stage: The sample is heated to a temperature of 2,800° C. for 10 seconds to evaporate the ashed inorganic ingredients. The inorganic ingredients undergo pyrolysis to be dissociated into atomic states. In FIG. 1, the incident measuring light ray 23 from the window 17 is absorbed into the inside of the cylindrical heating material 11 by atoms generated in the above described atomizing stage. The remaining light ray 22 is then transmitted to the outside of the electric furnace by window 16.

By the above described method, the concentrations of elements dissolved in the sample water drop 20, such as the cadmium element, are measured.

The prior art heretofore described has the following problems:

(1) The time required for drying is long: In the above described heating program for drying, ashing and atomizing the liquid drop 20 of 20 $\mu$l injected into the cylindrical heating material 11 of the electric furnace of the prior art shown in FIG. 1, the time required for drying is 60 seconds. If the liquid drop 20 is suddenly boiled and scattered in the drying process, the scattered liquid drop sticks to internal walls of the electrodes 12 and 13 or sticks to internal faces of the windows 16 and 17. Since the temperature is comparatively low at these portions, it is impossible to dry the sample in 60 seconds. The subsequent ashing and atomizing stages cannot be substantially performed. In the drying stage, therefore, the temperature must be set to such a temperature that the liquid drop 20 will never be suddenly boiled, i.e., 90° C. which is sufficiently lower than the boiling point. As a result, it takes approximately 60 seconds for the liquid drop to be dried. In the subsequent ashing stage and the atomizing stage, the temperature can be set to a high value because the sudden boiling phenomenon does not occur. Accordingly, the duration of each of the ashing stage and the atomizing stage is as short as 10 seconds.

Since the drying time is as long as 60 seconds as described above, it takes 80 seconds to analyze one sample. This results in a drawback that the analysis can be performed only 45 times at most in one hour. In reality, it takes approximately 10 seconds to inject the sample by using the micro-syringe, resulting in a further lowered work efficiency.

(2) The sensitivity of atomic absorption is low: In an atomic absorption spectrophotometer of the prior art, a well-known hollow cathode lamp is used as the light source. This lamp is filled with inert gas such as neon gas or argon gas with pressure typically ranging from 4 to 12 Torr. In the discharge state, the atomic spectrum of the cathode material is generated and emitted to the outside.

As is well known, profiles of the atomic emission line and atomic absorption line depend upon the atmosphere wherein the atoms are placed as well as the pressure and temperature of the gas. Measurement data obtained by experiments and theoretical formulas have been reported as follows.

As a report on the measurement of profiles of the atomic spectrum of a hollow cathode lamp and the atomic spectrum emitted from an acetylene flame placed in the atmospheric pressure, the following literature can be mentioned: [1] H. C. Wagenaar. and L. de Galan, Spectrochimica Acta, Vol. 28B, pp. 157–177 (1973).

As a report on the measurement of the relationship between the profile of the atomic spectrum of a light source and the atomic absorption efficiency, the following literature can be mentioned: [2] K. Yasuda, Anal. chem, Vol. 38, pp. 592–599 (1966).

As a known example of measurement of dependence of the profile upon the degree of vacuum, the following literature can be mentioned. Within a room having a degree of vacuum adjustable in the range of 50 to 760 Torr by the connection of a vacuum pump, oxygen and acetylene were burned with mixed flames. Zinc (Zn) atoms were introduced into the flames and the profile of the atomic absorption line of Zn-307.509 nm of zinc was measured. Dependence of this profile upon the degree of vacuum was thus measured. [3] T. J. Hollander and H. P. Broida, Combustion and Flame, Vol. 13, pp. 63 to 70 (1969).

The contents of these literature items can be summarized as follows: As the pressure of the atmospheric gas is raised, the breadth of the atomic spectrum is widened (as described in literature item [3]) and the peak of the spectrum is shifted into the longer wavelength direction.

In literature item [1], the atomic spectrum at a wavelength of 396.1 nm of aluminum emitted from a hollow cathode lamp is compared with that emitted from acetylene flames burning in the atmospheric pressure (760 Torr) as shown in FIG. 4. In FIG. 4, the ordinate represents the intensity of light in a relative scale. The abscissa represents the frequency of light. In FIG. 4, $\alpha$ represents low-pressure emission line of Al 396.1 nm emitted from a hollow cathode lamp with pressure of 8 Torr, while $\beta$ represents the atmospheric-pressure emission line of the same Al 396.1 nm emitted from acetylene flames with pressure of 760 Torr.

According to literature item [1], the atomic spectrum of Al 396.1 nm emitted from a hollow cathode lamp has a breadth of $86\pm1$ ($\times 10^{-3}$ cm$^{-1}$). The atomic spectrum of the same Al 396.1 nm emitted from acetylene flames burning in the atmospheric pressure have a breadth of $301\pm3$ ($\times 10^{-3}$ cm$^{-1}$). In addition, the latter is shifted by $48\pm2$ ($\times 10^{-3}$ cm$^{-1}$) in the longer wavelength direction (i.e., in the lower frequency direction) as compared with the former one.

The efficiency of light absorption by atoms becomes the highest when the profile of the absorption line of the atoms to be analyzed coincides with that of the emission line of the atoms used as the light source.

In the prior art apparatus shown in FIGS. 1 and 2, therefore, the emitting atoms exist in a hollow cathode lamp having a pressure of 8 Torr, and atoms to be analyzed exist in an electric furnace operating in the atmosphere of argon gas.

When aluminum (Al), for example, is analyzed by using this apparatus, the relationship between the emission line of the light source and the absorption line of the sample atoms is extremely close to that shown in FIG. 4. Absorption is caused only in the portion where the two spectra overlap each other. It is understood that the efficiency of absorption of light, i.e., the sensitivity of the atomic absorption, is largely lowered because of large discrepancy between both spectra.

SUMMARY OF THE INVENTION

The present invention has been obtained in view of these circumstances. An object of the present invention is to provide an atomic absorption spectrophotometer capable of shortening the analysis work time and raising the sensitivity of the atomic absorption.

In accordance with the present invention, therefore, atomic absorption spectrophotometer using spectrophotometry is performed a method of including the steps of using a low-pressure atmosphere lamp emitting an atomic spectrum as the light source, applying the light ray emitted from the light source to atomic vapor generated in an electric furnace for drying, ashing and atomizing an injected liquid drop of the analysis sample having a predetermined volume, applying the transmitted light ray to a monochromator, selecting a light ray having a wavelength of an atomic absorption line absorbed by atoms to be analyzed. The atomic absorption spectrophotometer utilized is so configured that the above described electric furnace will have an air-tight structure allowing the vacuum evacuation and the spectrophotometer will include means for heating the above described liquid drop to dry, ash and atomize it in the above described vacuum evacuation stage.

By thus making the electric furnace so as to allow vacuum evacuation, it is possible to make the evaporation speed of the sample water drop in the above described electric furnace extremely high. It is also possible to largely improve the atomic absorption efficiency.

BRIEF DESCRIPTION OF THE DRAWINGS

FIGS. 1 and 2 are a longitudinal sectional view showing an example of the structure of a conventional prior art electric furnace and a front view, seen from the axis direction, of that prior art furnace respectively.

FIG. 3 shows a conventional prior art heating program.

FIGS. 6 and 7 are a longitudinal sectional view showing an example of the structure of an electric furnace according to the present invention and a front view, seen from the axis direction, of that furnace, respectively.

FIGS. 8 and 9 show a heating program according to the present invention.

DESCRIPTION OF THE PREFERRED EMBODIMENTS

The present invention will now be described in detail by referring to drawings.

Figure 5:
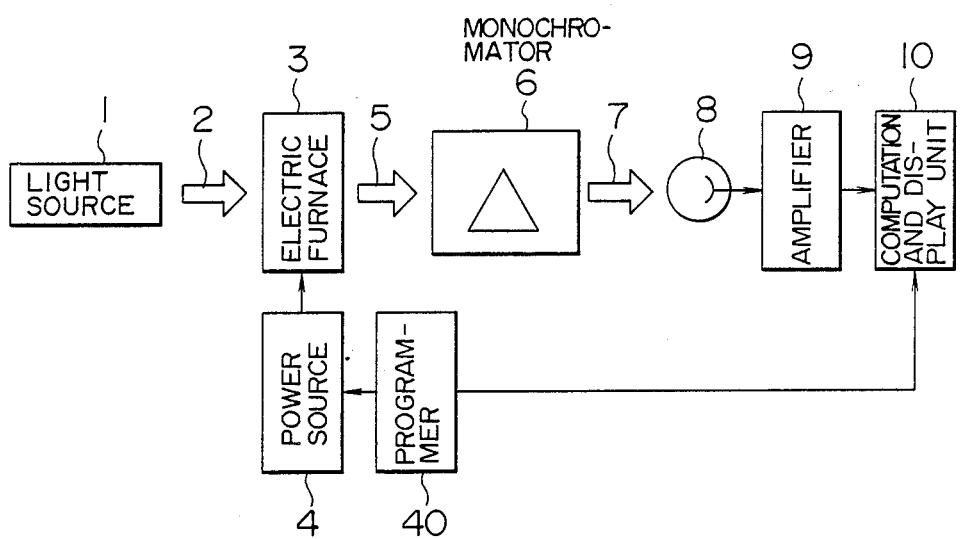
FIG. 5 is a block diagram showing an embodiment of the entire configuration according to the present invention.

In FIG. 5, a light ray 2 emitted from a light source 1 comprising a hollow cathode lamp is applied into an electric furnace 3 having an analysis sample introduced therein. A power source 4 for supplying heating power is connected to the above described electric furnace 3. A liquid drop of an analysis sample introduced into this electric furnace 3 is dried, ashed and then heated to a high temperature to be evaporated into the atomic state by the power source 4 controlled by a programmer 40. The incident light ray 2 to the electric furnace 3 is partially absorbed by the atomized vapor. The remaining transmitted light ray 5 is applied to a monochromator 6. An atomic absorption line 7 is selected in the monochromator 6 and applied to a photoelectric converter 8. An electric signal proportionate to the intensity of the atomic absorption line 7 is sent to an amplifier 9. Finally in a computation and display unit 10, computation of the signal sent from the amplifier 9 is performed. Numerical values proportionate to the density of the atomic vapor of the analysis sample generated in the electric furnace 3 are derived and displayed as the result of the analysis.

FIGS. 6 and 7 are structure diagrams showing an embodiment of the atomic absorption spectrophotometer according to the present invention. In particular, FIGS. 6 and 7 mainly show its electric furnace. The same numerals as those of FIGS. 1 and 2 denote identical materials.

In FIGS. 6 and 7, a cylindrical heating material 11 is put between a right-hand electrode 12 and a left-hand electrode 13 and electrically connected to these electrodes. A current is supplied through a right-hand terminal 14 and a left-hand terminal 15 to heat the cylindrical heating material 11.

The above described right-hand electrode 12 has a window 16 comprising a quartz material, for example, and transmitting a light ray used for the atomic absorption measurement.

The left-hand electrode 13 also has a window 17 for the incidence of a light ray 23.

A cylinder 18, comprising an electrical insulator, is put on the right-hand electrode 12 and the left-hand electrode 13. Airtightness of the contacting portion of both electrodes is maintained by airtight O rings 24 and 25.

A vacuum evacuation pump 29 is connected to the right-hand electrode 12 via a valve 28.

The central part of the cylinder 18 has an opening 19 for introducing a sample to be analyzed. The cylindrical heating material 11 also has an opening 26. A liquid drop 20 of 20 μl, for example, is injected into the inside of the cylindrical heating material 11 via the openings 19 and 26 by using a micro-syringe, for example. Thereafter, a lid 27 which can be opened and shut is shut in order to maintain the airtightness of the inside.

Air inside the cylindrical heating material 11 is evacuated by opening the valve 28 and activating the vacuum evacuation pump 29.

The relationship between the current supplied to the cylindrical heating material 11 and the temperature of the cylindrical heating material 11 is empirically derived beforehand. A predetermined heating program is programmed within a programmer 40 shown in FIG. 5. The cylindrical heating material 11 of FIG. 6 is heated by this heating program.

Figure 9:
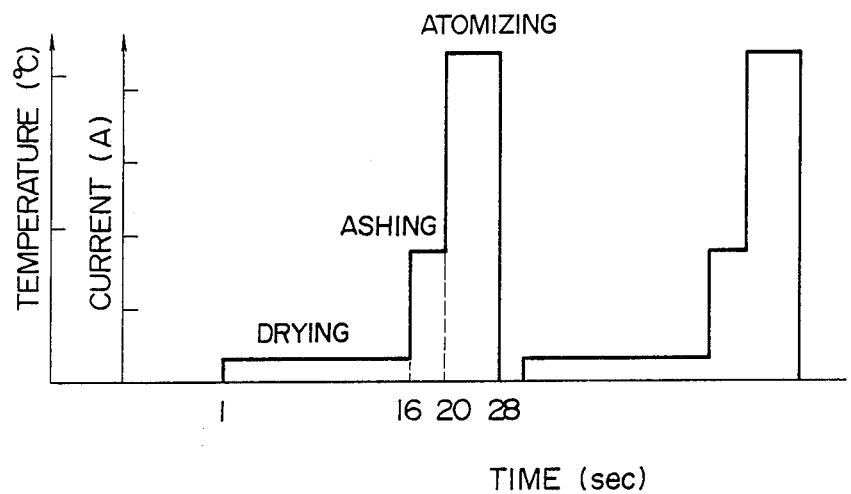

FIGS. 8 and 9 show the heating program stored in the programmer 40 for performing the atomic absorption measurement by using the electric furnace shown in FIG. 6.

As shown in FIGS. 8 and 9, the heating program is divided into three stages, i.e., drying, ashing and atomizing stages. The heating program is defined by the temperature to which the cylindrical heating material 11 is heated and the time it is maintained at that temperature.

First of all, the vacuum evacuation pump 29 shown in FIG. 6, such as an oil rotary pump, starts its operation. Subsequently, the valve 28 is opened and the inside of the cylindrical heating material 11 is evacuated to a degree of vacuum of, say, 8 Torr. It is sufficient that the degree of vacuum is sufficiently smaller than the atmospheric pressure of 760 Torr. As a result, it is possible to sufficiently promote the evaporation of the sample solution and reduce the width of the absorption spectra to raise the atomic absorption sensitivity.

Subsequently, the heating program is started. The heating program is advanced by changing the current supplied to the cylindrical heating material 11 from power source 4 through terminals 14 and 15 by means of the programmer 40 shown in FIG. 5 in accordance with the program shown in FIGS. 8 and 9. In the latter half of the atomizing stage, the programmer 40 makes the computation display unit 10 perform the processing of measured signals to obtain the atomic absorption signal of the element to be analyzed.

The following effects are obtained by using such an atomic absorption spectrophotometer:

(1) Shortening of heating program time.

Since the inside of the cylindrical heating material 11 shown in FIG. 6 is kept at 8 Torr in degree of vacuum, the evaporation speed of the sample water drop 20 is extremely increased as compared with the case of the atmospheric pressure (760 Torr) shown in FIG. 1. The drying time shown in FIG. 8 is shortened to approximately one fourth, i.e., 16 seconds. Since the ashing stage mainly depends upon the temperature rather than the pressure of the atmosphere, its shortening is smaller than that of the drying stage. Nevertheless the ashing stage is shortened to approximately half.

In the atomizing stage, the temperature at which the chemical compound of the element to be analyzed is evaporated takes precedence over the pressure of the atmosphere. Accordingly, the effect of time shortening in the atomizing stage is relatively small.

As compared with the example of the prior art shown in FIG. 3, however, the total time of the drying, ashing and atomizing stages is shortened to approximately one third, i.e., 28 seconds.

(2) Enhancement in atomic absorption sensitivity.

Figure 10:
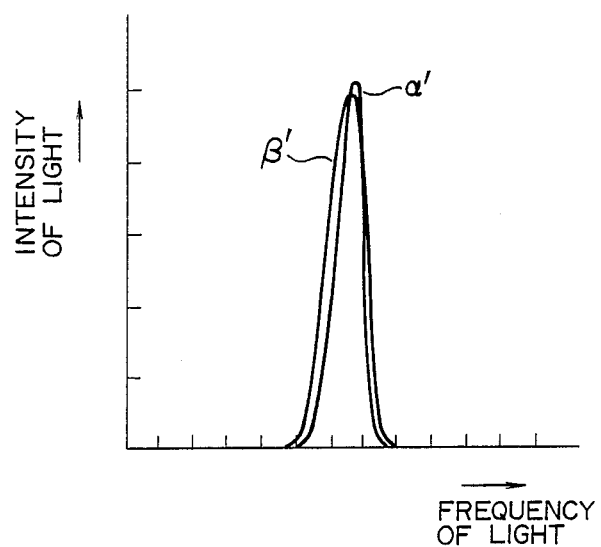
FIG. 10 shows an example of spectrum characteristic according to the present invention.

In FIG. 10, the ordinate represents the intensity of the light in relative value. The abscissa represents the frequency ($cm^{-1}$) of the light. In FIG. 10, $\alpha'$ represents the low-pressure emission line of Al 396.1 nm emitted from a hollow cathode lamp with pressure of 8 Torr, while $\beta'$ represents the low-pressure absorption line of Al 396.1 nm in the electric furnace with pressure of 8 Torr and temperature of 2,800° C. Since the temperature 2,800° C. of the electric furnace is higher than the temperature close to 400° C. of the hollow cathode lamp in the discharge state, the absorption line $\beta'$ is somewhat shifted in the low frequency side as compared with the absorption line $\beta'$. Since the pressure values of the atmosphere in which the atoms are placed are equal to each other, however, the overlapping portion of both spectra is far larger than that of FIG. 4. It is thus understood that the efficiency of atomic absorption is largely improved. Even if the pressure of the electric furnace is not close to 8 Torr, the sensitivity of the atomic absorption is largely improved as compared with the case of the atmospheric pressure shown in FIG. 4, so long as the pressure of the electric furnace is sufficiently lower than the atmospheric pressure of 760 Torr. It is a matter of course that the valve 28 may be provided with a leak valve to maintain a predetermined pressure of approximately 8 Torr.

(3) Degree of improvement in analysis performance.

Figure 4:
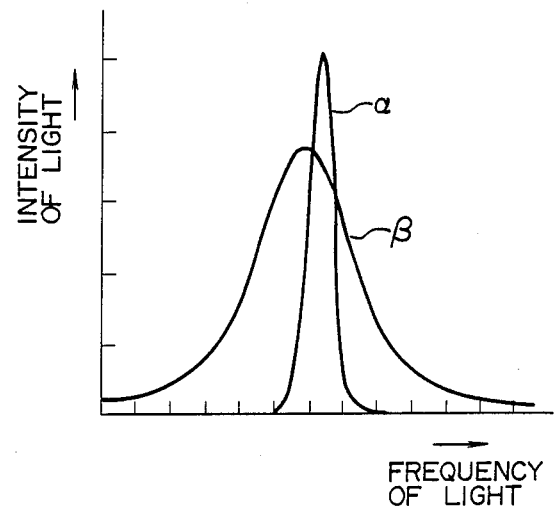
FIG. 4 shows conventional spectra characteristics.
Figure 11:
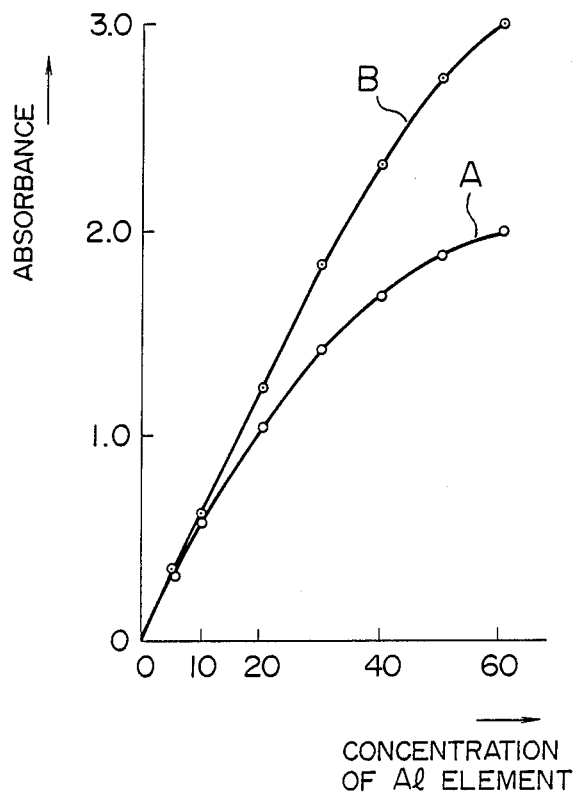
FIG. 11 shows measurement results according to the present invention in comparison with those of the prior art.

In FIG. 11, the ordinate represents the absorbance and the abscissa represents the concentration (ppm) of aluminum (Al) element in a sample. In FIG. 11, A denotes a calibration curve for Al 396.1 nm obtained when the electric furnace of the prior art shown in FIG. 2 is used. In the prior art apparatus, there is large discrepancy between the emission line α and the absorption line β as shown in FIG. 4. Therefore, the calibration curve A of FIG. 11 approaches the saturation state at a value of absorbance close to 2.0. This fact can be understood from the above described literature item [2]. However, a calibration curve B of Al 396.1 nm, obtained when the electric furnace shown in FIG. 6 according to the present embodiment is used, is approximately linear until the absorbance reaches 3.0. In addition, the efficiency of the atomic absorption, i.e., the sensitivity, is improved by approximately 1.4 times as compared with the calibration curve A of the prior art apparatus when the concentration of Al in the sample is 60 ppm.

(4) Other effects.

Since the inside of the electric furnace has a relatively high degree of vacuum in accordance with the present invention, waste of the cylindrical heating material comprising graphite, caused by its reaction with oxygen in high temperature heating, is largely reduced. The use of inert gas, such as argon gas, can thus be reduced or omitted. In addition, sticking of vapor caused by sudden boiling of the sample onto the internal wall faces of the electric furnace and the cylindrical heating material is largely reduced.

We claim:

1. An atomic absorption spectrophotometer including:
    an electric furnace for drying and ashing a liquid sample to be analyzed and then atomizing the sample to generate atomic vapor;
    a low-pressure lamp for emitting light having a spectrum of an element to be analyzed onto the atomic vapor atomized in said electric furnace;
    a monochromator for splitting the transmitted light from said electric furnace and selecting a wavelength of an atomic absorption line absorbed by said element to be analyzed; and
    a signal processing unit for detecting light having the selected wavelength supplied from said monochromator and for analyzing the element to be analyzed,
    wherein said electric furnace comprises: a sealing mechanism for maintaining the inside of said electric furnace airtight; and
    an evacuation unit for evacuating the inside of said electric furnace to a pressure equal or near to the pressure of the inside of said lamp.

2. An atomic absorption spectrophotometer according to claim 1, wherein said electric furnace has an aperture for introducing a sample into said electric furnace and said sealing mechanism includes a lid for opening and shutting said aperture.

3. An atomic absorption spectrophotometer according to claim 1, wherein said sealing mechanism includes a valve through which said evacuation unit is connected to the inside of said electric furnace.

4. An atomic absorption spectrophotometer according to claim 1, wherein said evacuation unit evacuates the inside of said electric furnace to attain the pressure when drying the liquid sample and to attain the pressure equal or near to that of the inside of said lamp at least when atomizing said sample to generate atomic vapor.

5. An atomic absorption photometric analysis method comprising:
    injecting a liquid sample to be analyzed into the interior of an electric furnace;
    sealing the electric furnace to make the interior thereof airtight;
    reducing the pressure within the interior of the electric furnace;
    heating the interior of the electric furnace to a first temperature for a first time duration to dry the liquid sample to a dried solute;
    heating the interior of the electric furnace to a second temperature, higher than the first temperature, for a second time duration to ash organic matters included in the dried solute, leaving ashed inorganic ingredients;
    heating the interior of the electric furnace to a third temperature, higher than the second temperature, for a third time duration to evaporate the ashed inorganic ingredients and to cause the inorganic ingredients to undergo pyrolysis, dissociating into atomic states;
    energizing a light source filled with inert gas at a pressure equal or near to the reduced pressure within the interior of the electric furnace, to emit light at a spectrum that is absorbed by the atomized sample;
    passing the emitted light through the interior of the electric furnace;
    detecting light passing from the interior of the electric furnace;
    converting the detected light into an electric signal indicative of the atomic absorption of light within the interior of the electric furnace; and
    applying the electric signal to a display device to display an indication of the density of the atomic vapor of the liquid sample.

6. A method as claimed in claim 5 wherein the pressure within the interior of the electric furnace is reduced to 8 Torr.

7. A method as claimed in claim 6 wherein the first temperature is 90° C., the first time is 16 seconds, the second temperature is 600° C., the second time is 4 seconds, the third temperature is 2800° C., and the third time is 8 seconds.

* * * * *